United States Patent
Song et al.

(10) Patent No.: US 9,397,229 B2
(45) Date of Patent: Jul. 19, 2016

(54) NANO RESONANCE APPARATUS AND METHOD

(71) Applicants: Samsung Electronics Co., Ltd., Suwon-si (KR); Korea University Industrial & Academic Collaboration Foundation, Seoul (KR)

(72) Inventors: In Sang Song, Osan-si (KR); Ho Soo Park, Yongin-si (KR); Duck Hwan Kim, Goyang-si (KR); Sang Uk Son, Yongin-si (KR); Jae Shik Shin, Hwaseong-si (KR); Jae-Sung Rieh, Seoul (KR); Byeong Kwon Ju, Seoul (KR); Dong Hoon Hwang, Seoul (KR)

(73) Assignees: Samsung Electronics Co., Ltd., Suwon-si (KR); Korea University Industrial & Academic Collaboration Foundation, Seoul (KR)

( * ) Notice: Subject to any disclaimer, the term of this patent is extended or adjusted under 35 U.S.C. 154(b) by 0 days.

(21) Appl. No.: 14/057,590

(22) Filed: Oct. 18, 2013

(65) Prior Publication Data
US 2014/0110763 A1    Apr. 24, 2014

(30) Foreign Application Priority Data
Oct. 24, 2012  (KR) .................. 10-2012-0118435

(51) Int. Cl.
| | |
|---|---|
| *H01L 29/82* | (2006.01) |
| *G01N 29/02* | (2006.01) |
| *G01N 29/036* | (2006.01) |
| *H01L 29/78* | (2006.01) |
| *B81B 3/00* | (2006.01) |
| *B82Y 25/00* | (2011.01) |
| *H01L 29/423* | (2006.01) |
| *H01L 29/06* | (2006.01) |

(52) U.S. Cl.
CPC .............. *H01L 29/82* (2013.01); *B81B 3/0078* (2013.01); *G01N 29/022* (2013.01); *G01N 29/036* (2013.01); *H01L 29/78* (2013.01); *B81B 2201/0271* (2013.01); *B82Y 25/00* (2013.01); *H01L 29/0673* (2013.01);
(Continued)

(58) Field of Classification Search
CPC ................................. H01L 29/82; B82Y 10/00
USPC .................................. 257/252; 977/762, 938
See application file for complete search history.

(56) References Cited

U.S. PATENT DOCUMENTS

| | | | | |
|---|---|---|---|---|
| 4,979,149 A | * | 12/1990 | Popovic .................. | G11C 11/24 257/368 |
| 7,349,236 B2 | * | 3/2008 | Lin ........................ | B82Y 10/00 365/129 |

(Continued)

FOREIGN PATENT DOCUMENTS

| | | |
|---|---|---|
| JP | 2009-268084 A | 11/2009 |
| KR | 10-2011-0044799 A | 4/2011 |

(Continued)

OTHER PUBLICATIONS

A. Ionescu, "Vibrating Body Transistors: Enabling Fin-FET Nano-Electro-Mechanical Resonators," *Proceedings of the 2010 IEEE International Frequency Control Symposium*, p. 333, Jan. 1-4, 2010, Newport Beach, California.

*Primary Examiner* — Fernando L Toledo
*Assistant Examiner* — Neil Prasad
(74) *Attorney, Agent, or Firm* — NSIP Law

(57) ABSTRACT

A nano resonance apparatus includes a gate electrode configured to generate a magnetic field, and a nanowire connecting a source electrode to a drain electrode and configured to vibrate in the presence of the magnetic field. The nanowire includes a protruding portion extending in a direction of the gate electrode.

16 Claims, 7 Drawing Sheets

(52) U.S. Cl.
CPC ....... *H01L 29/42372* (2013.01); *Y10S 977/762* (2013.01); *Y10S 977/938* (2013.01)

(56) References Cited

U.S. PATENT DOCUMENTS

| | | | |
|---|---|---|---|
| 7,358,648 B2 * | 4/2008 | Nakamura | H03H 3/0078 310/333 |
| 7,579,618 B2 | 8/2009 | Adam | |
| 2010/0214034 A1 * | 8/2010 | Peng et al. | 331/154 |
| 2010/0219895 A1 | 9/2010 | Duraffourg et al. | |
| 2011/0167913 A1 | 7/2011 | Bennahmias et al. | |
| 2011/0212535 A1 | 9/2011 | Kaul et al. | |
| 2012/0126327 A1 * | 5/2012 | Song et al. | 257/365 |
| 2013/0048950 A1 * | 2/2013 | Levy et al. | 257/29 |

FOREIGN PATENT DOCUMENTS

| | | |
|---|---|---|
| KR | 10-2011-0080392 A | 7/2011 |
| KR | 10-2011-0113847 A | 10/2011 |
| KR | 10-2011-0126373 A | 11/2011 |

\* cited by examiner

Case 1  Case 2

Case 1          Case 2

NANO RESONANCE APPARATUS AND METHOD

CROSS-REFERENCE TO RELATED APPLICATIONS

This application claims the benefit under 35 USC 119(a) of Korean Patent Application No. 10-2012-0118435 filed on Oct. 24, 2012, in the Korean Intellectual Property Office, the entire disclosure of which is incorporated herein by reference for all purposes.

BACKGROUND

1. Field

This description relates to a nano resonance apparatus including at least one protruding portion of a gate electrode or a nanowire, and a nano resonance method.

2. Description of Related Art

A nano resonance apparatus has a high sensitivity at a high frequency as well as at a low frequency, a short response time, and a low power consumption, and thus has various applications in the field of the nano-bio health care industry.

Generally, as the size of a nano resonance apparatus increases, a 0-factor of the nano resonance apparatus increases. As a consequence, sensitivity is also increased. However, when the size of the nano resonance apparatus is increased, a resonant frequency is reduced, which allows the nano resonance apparatus to operate at a low frequency only. Conversely, when the size of the nano resonance apparatus is decreased, the resonant frequency increases, but the 0-factor of the nano resonance apparatus decreases, and consequently, sensitivity is reduced.

SUMMARY

In one general aspect, a nano resonance apparatus includes a gate electrode configured to generate a magnetic field; and a nanowire connecting a source electrode to a drain electrode and configured to vibrate in the presence of the magnetic field; wherein the nanowire includes a protruding portion extending in a direction of the gate electrode.

The gate electrode may include an indented portion corresponding to the protruding portion of the nanowire.

The protruding portion may have a shape of at least one polygon or at least one curve.

The gate electrode may be disposed adjacent to one side of the nanowire, or the gate electrode may be one of a plurality of gate electrodes disposed adjacent to a plurality of sides of the nanowire.

The nanowire may be spaced a predetermined distance or more apart from a substrate on which the source electrode and the drain electrode are disposed.

The gate electrode may be disposed between the substrate and the nanowire.

In another general aspect, a nano resonance apparatus includes a nanowire connecting a source electrode to a drain electrode; and a gate electrode configured to generate a magnetic field and to vibrate with the nanowire in the presence of the magnetic field; wherein the gate electrode includes at least one protruding portion extending in a direction of the nanowire.

The nanowire may include at least one indented portion corresponding to the at least one protruding portion of the gate electrode.

In another general aspect, a nano resonance apparatus includes a gate electrode configured to generate a magnetic field; and a nanowire connecting a source electrode to a drain electrode and configured to vibrate with the gate electrode in the presence of the magnetic field; wherein the gate electrode includes at least one protruding portion extending in a direction of the nanowire.

The nanowire may include at least one indented portion corresponding to the at least one protruding portion of the gate electrode.

In another general aspect, a nano resonance apparatus includes a gate electrode configured to generate a magnetic field; and a nanowire connecting a source electrode to a drain electrode and configured to vibrate with the gate electrode in the presence of the magnetic field; wherein the nanowire includes at least one protruding portion extending in a direction of the gate electrode.

The gate electrode may include at least one indented portion corresponding to the at least one protruding portion of the nanowire.

In another general aspect, a nano resonance method performed by a nano resonance apparatus includes generating a magnetic field using a gate electrode of the nano resonance apparatus; and vibrating a nanowire of the nano resonance apparatus in the presence of the magnetic field; wherein the nanowire includes at least one protruding portion extending in a direction of the gate electrode.

In another general aspect, a nano resonance method performed by a nano resonance apparatus includes generating a magnetic field using a gate electrode of the nano resonance apparatus; and vibrating the gate electrode of the nano resonance apparatus in the presence of the magnetic field; wherein the gate electrode includes at least one protruding portion extending in a direction of a nanowire of the nano resonance apparatus.

In another general aspect, a nano resonance method performed by a nano resonance apparatus includes generating a magnetic field using a gate electrode of the nano resonance apparatus; and vibrating the gate electrode of the nano resonance apparatus with a nanowire of the nano resonance apparatus in the presence of the magnetic field; wherein the gate electrode includes at least one protruding portion extending in a direction of the nanowire.

In another general aspect, a nano resonance method performed by a nano resonance apparatus includes generating a magnetic field using a gate electrode of the nano resonance apparatus; and vibrating a nanowire of the nano resonance apparatus with the gate electrode of the nano resonance apparatus in the presence of the magnetic field; wherein the nanowire includes at least one protruding portion extending in a direction of the gate electrode.

In another general aspect, a nano resonance apparatus includes a gate electrode configured to generate a magnetic field; and a nanowire; wherein the gate electrode includes a protruding portion extending in a direction of the nanowire, and the nanowire does not include a protruding portion or an indented portion; or the nanowire includes a protruding portion extending in a direction of the gate electrode, and the gate electrode does not include a protruding portion or an indented portion; or the gate electrode includes a protruding portion extending in a direction of the nanowire, and the nanowire includes an indented portion corresponding to the protruding portion of the gate electrode; or the nanowire includes a protruding portion extending in a direction of the gate electrode, and the gate electrode includes an indented portion corresponding to the protruding portion of the nanowire.

The nanowire may be configured to vibrate in the presence of the magnetic field, and the gate electrode may be configured to not vibrate in the presence of the magnetic field; or the gate electrode may be configured to vibrate in the presence of the magnetic field, and the nanowire may be configured to not vibrate in the presence of the magnetic field; or the nanowire and the gate electrode may be configured to vibrate with one another in the presence of the magnetic field.

The nano resonance apparatus may further include a source electrode; and a drain electrode; and the nanowire may connect the source electrode to the drain electrode.

The gate electrode may be a first gate electrode; the nano resonance apparatus may further include a second gate electrode; and the first gate electrode may be spaced apart from the nanowire in a first direction, and the second gate electrode may be spaced apart from the nanowire in a second direction substantially opposite to the first direction; or the first gate electrode may be spaced apart from the nanowire in a first direction, and the second gate electrode may be spaced apart from the nanowire in a second direction substantially perpendicular to the first direction.

Other features and aspects will be apparent from the following detailed description, the drawings, and the claims.

DETAILED DESCRIPTION

Figure 1:
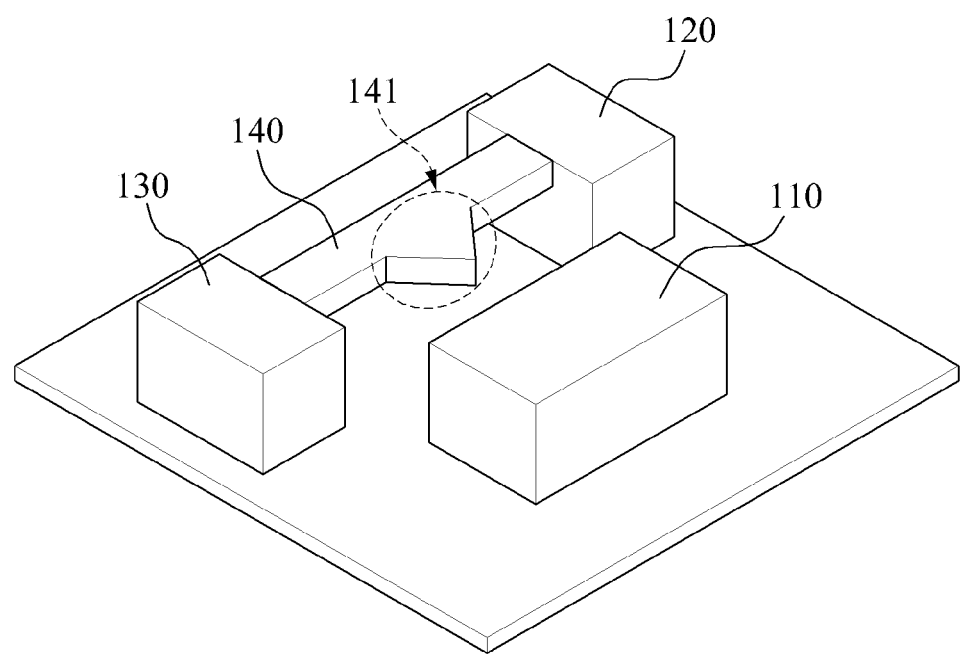
FIG. 1 is a diagram illustrating an example a structure of a nano resonance apparatus.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

In this description, the phrase "an indented portion corresponding to a protruding portion" indicates that for a protruding portion on one element, there is a corresponding indented portion on another element. The corresponding indented portion on the other element faces the protruding portion on the one element. The corresponding indented portion may have the same size and shape as the protruding portion so that the protruding portion would mesh with the corresponding indented portion if the protruding portion were inserted into the corresponding indented portion. Alternatively, the corresponding indented portion may have a different size and/or a different shape than the protruding portion.

FIG. 1 is a diagram illustrating an example a structure of a nano resonance apparatus. Referring to FIG. 1, the nano resonance apparatus includes a gate electrode 110, a source electrode 120, a drain electrode 130, and a nanowire 140. The nano resonance apparatus of FIG. 1 is a vibrating body type nano resonator.

The nanowire 140 connects the source electrode 120 to the drain electrode 130, and vibrates in the presence of a magnetic field generated by the gate electrode 110. To enable the vibration of the nanowire 140 in the presence of the magnetic field generated by the gate electrode 110, the nanowire 140 is spaced a predetermined distance or more apart from a substrate on which the source electrode 120 and the drain electrode 130 are disposed.

The nanowire 140 includes at least one protruding portion 141 extending in a direction of the gate electrode 110 to increase a surface area of the nanowire 140 facing the gate electrode 110. In the example in FIG. 1, the gate electrode 110 does not include a protruding portion or an indented portion, but the gate electrode 110 is not limited to such a form. For example, the gate electrode 110 may include an indented portion corresponding to the protruding portion 141 of the nanowire 140 to increase a surface area of the gate electrode 110 facing the nanowire 140.

The protruding portion 141 of the nanowire 140 may have a shape of at least one polygon or at least one curve. Examples of the shape of the protruding portion 140 will be described in further detail with reference to FIG. 3.

As shown in FIG. 1, the gate electrode 110 is disposed adjacent to one side of the nanowire 140. However, a plurality of gate electrodes may be disposed adjacent to a plurality of sides of the nanowire 140. An example of a plurality of gate electrodes disposed adjacent to a plurality of sides of a nanowire will be described in further detail with reference to FIG. 11.

Also, the gate electrode 110 may be disposed between a substrate and the nanowire 140. An example of a gate electrode disposed between a substrate and a nanowire will be described in further detail with reference to FIG. 10.

The gate electrode 110 and the nanowire 140 may include any one or any combination of silicon (Si), germanium (Ge), poly-Si, amorphous silicon (a-Si), germanium-silicon (GeSi), and one or more Group III-Group V compounds.

The gate electrode 110, the source electrode 120, the drain electrode 130, and the nanowire 140 may be an n-type p-type material doped with an impurity ion. A nanowire manufacturing equipment may dope a nanowire with the impurity ion, and may make the doped nanowire extend in a direction of the gate electrode 110 to form the protruding portion 141.

The nano resonance apparatus improves a resonance sensitivity and a Q-factor by including the protruding portion 141 of the nanowire 140 to increase a surface area of the nanowire 140 facing the gate electrode 110.

Figure 2:
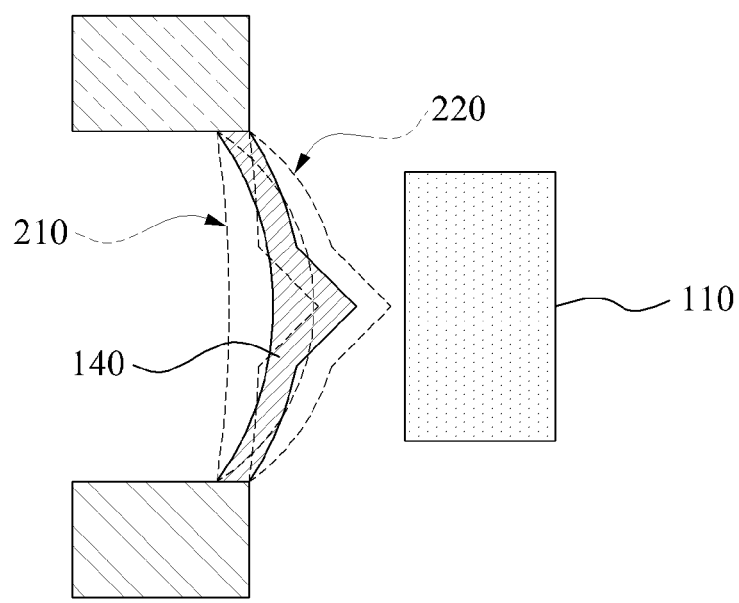
FIG. 2 is a diagram illustrating an example of operation of the nano resonance apparatus of FIG. 1.

FIG. 2 is a diagram illustrating an example of operation of the nano resonance apparatus of FIG. 1. The nanowire 140 of the nano resonance apparatus vibrates in the presence of the magnetic field generated by the gate electrode. The nanowire 140 is alternately attracted to the gate electrode 110 as indicated by reference numeral 220, and repelled from the gate electrode 110 as indicated by reference numeral 210, due to the presence of the magnetic field.

The nanowire 140 vibrates in the presence of the magnetic field with an increased sensitivity due to the increased surface area of the nanowire 140 facing the gate electrode 110 caused by the protruding portion 141 of the nanowire 140.

Figure 3:
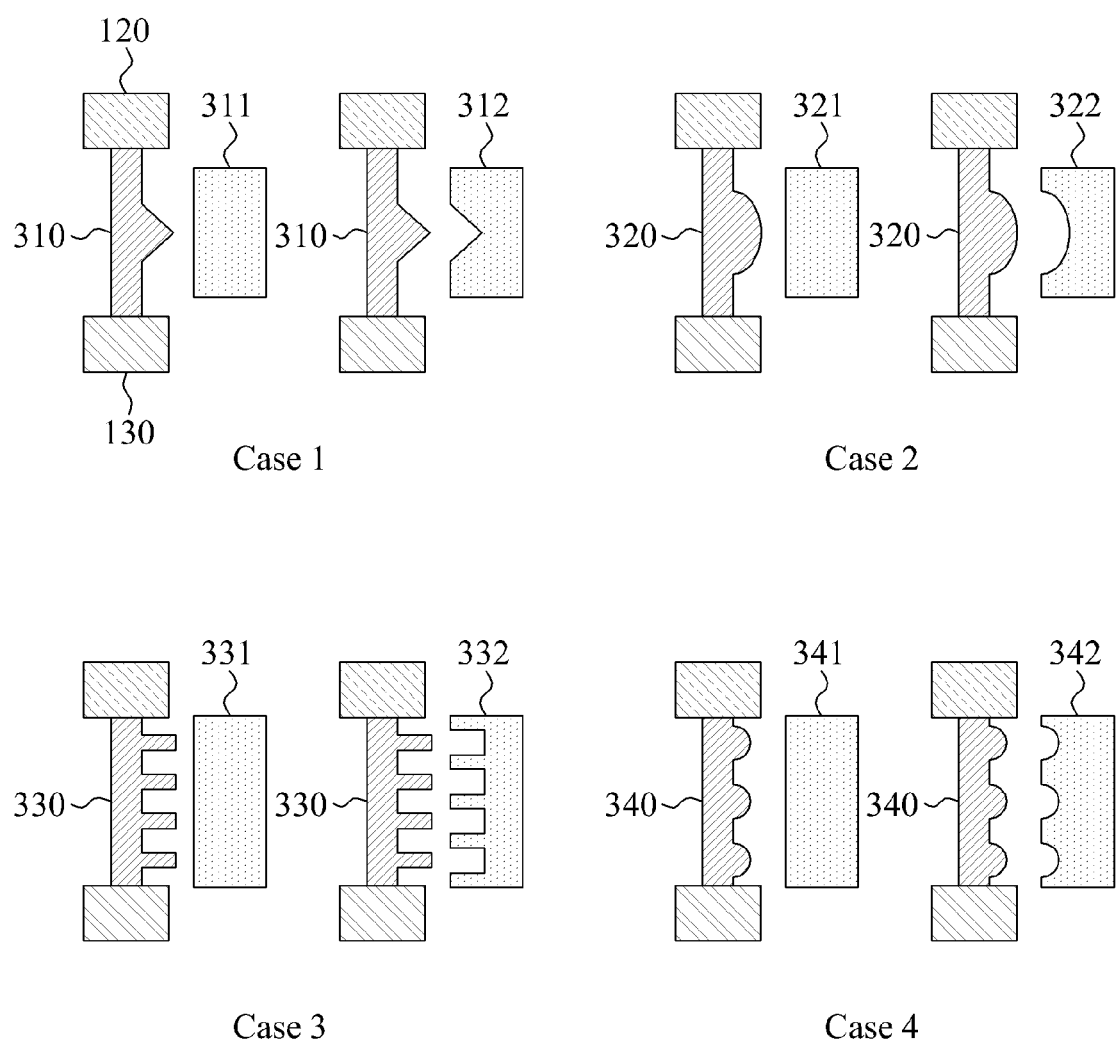
FIG. 3 is a diagram illustrating examples of a nanowire and a gate electrode of the nano resonance apparatus of FIG. 1.

FIG. 3 is a diagram illustrating examples of a nanowire and a gate electrode of the nano resonance apparatus of FIG. 1.

As shown in Case 1, a nanowire 310 includes a protruding portion having a shape of a triangle to increase a surface area of the nanowire 310 facing a gate electrode. A gate electrode 311 does not include a protruding portion or an indented portion, but a gate electrode 312 includes an indented portion corresponding to the protruding portion of the nanowire 310 to increase a surface area of the gate electrode 312 facing the nanowire 310.

As shown in Case 2, a nanowire 320 includes a protruding portion having a shape of a curve to increase a surface area of the nanowire 320 facing a gate electrode. A gate electrode 321 does not include a protruding portion or an indented portion, but a gate electrode 322 includes an indented portion corresponding to the protruding portion of the nanowire 320 to increase a surface area of the gate electrode 322 facing the nanowire 320.

As shown in Case 3, a nanowire 330 includes a protruding portion having a shape of a comb-like polygon to increase a surface area of the nanowire 330 facing a gate electrode. A gate electrode 331 does not include a protruding portion or an indented portion, but a gate electrode 332 includes an indented portion corresponding to the protruding portion of the nanowire 330 to increase a surface area of the gate electrode 332 facing the nanowire 330.

As shown in Case 4, a nanowire 340 includes a protruding portion consisting of a plurality of curves to increase a surface area of the nanowire 340 facing a gate electrode. A gate electrode 341 does not include a protruding portion or an indented portion, but a gate electrode 342 includes an indented portion corresponding to the protruding portion of the nanowire 340 to increase a surface area of the gate electrode 342 facing the nanowire 340.

Figure 4:
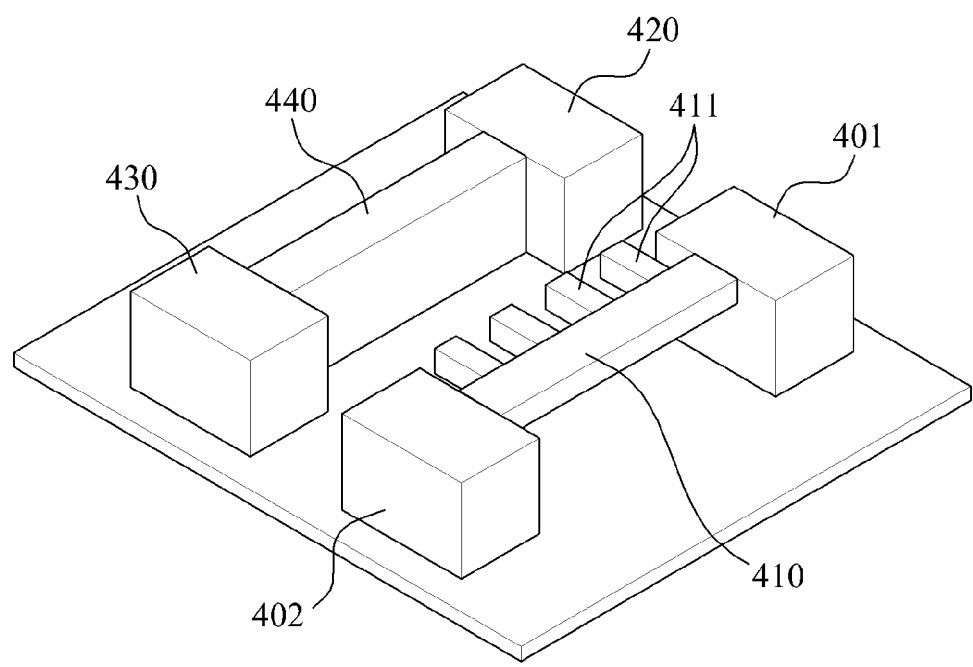
FIG. 4 is a diagram illustrating another example of a structure of a nano resonance apparatus.

FIG. 4 is a diagram illustrating another example of a structure of a nano resonance apparatus. Referring to FIG. 4, the nano resonance apparatus includes a gate electrode 410, a source electrode 420, a drain electrode 430, and a nanowire 440. The nano resonance apparatus of FIG. 4 is a suspended gate type nano resonator.

The gate electrode 410 includes at least one protruding portion 411 extending in a direction of the nanowire 440 to increase a surface area of the gate electrode 410 facing the nanowire 440. The at least one protruding portion 411 may have a shape of at least one polygon or at least one curve. The shape of the at least one protruding portion 411 will be described in further detail with reference to FIG. 6.

The gate electrode 410 generates a magnetic field, and vibrates with the nanowire 440 in the presence of the magnetic field. To enable the vibration of the gate electrode 410 with the nanowire 440 in the presence of the magnetic field, the gate electrode 410 is spaced a predetermined distance or more apart from a substrate on which the source electrode 420, the drain electrode 430, and the nanowire 440 are disposed. A supporting unit is provided on the substrate to support the gate electrode 410 at the predetermined distance or more apart from the substrate. In the example in FIG. 4, the supporting unit includes a first supporting unit 401 and a second supporting unit 402.

The nanowire 440 connects the source electrode 420 to the drain electrode 430. The nanowire 440 does not include a protruding portion or an indented portion, but the nanowire 440 is not limited to such a form. For example, the nanowire 441 may include an indented portion corresponding to at least one the protruding portion 411 of the gate electrode 410 to increase a surface area of the nanowire 441 facing the gate electrode 410.

The nano resonance apparatus improves a resonance sensitivity and a Q-factor by including the at least one protruding portion 411 of the gate electrode 410 to increase a surface area of the gate electrode 410 facing the nanowire 440.

Figure 5:
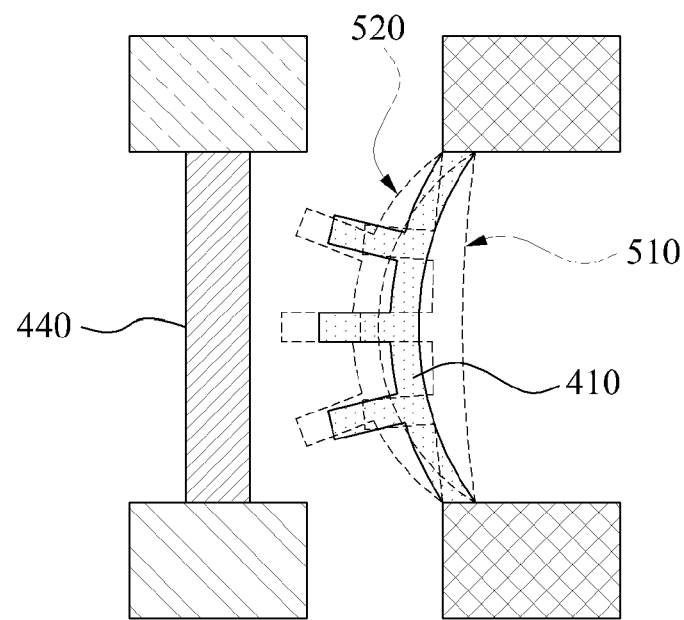
FIG. 5 is a diagram illustrating an example of operation of the nano resonance apparatus of FIG. 4.

FIG. 5 is a diagram illustrating an example of operation of the nano resonance apparatus of FIG. 4. The gate electrode 410 of the nano resonance apparatus generates a magnetic field, and vibrates in the presence of the magnetic field while the nanowire is fixed to the substrate. The gate electrode 410 is alternately attracted to the nanowire 440 as indicated by reference numeral 520, and repelled from the nanowire 440 as indicated by reference numeral 510, due to the presence of the magnetic field.

The gate electrode 410 vibrates with an increased sensitivity in the presence of the magnetic field generated by the gate electrode 410 due to the increased surface area of the gate electrode 410 facing the nanowire 440 caused by the at least one protruding portion 411 of the gate electrode 410.

Figure 6:
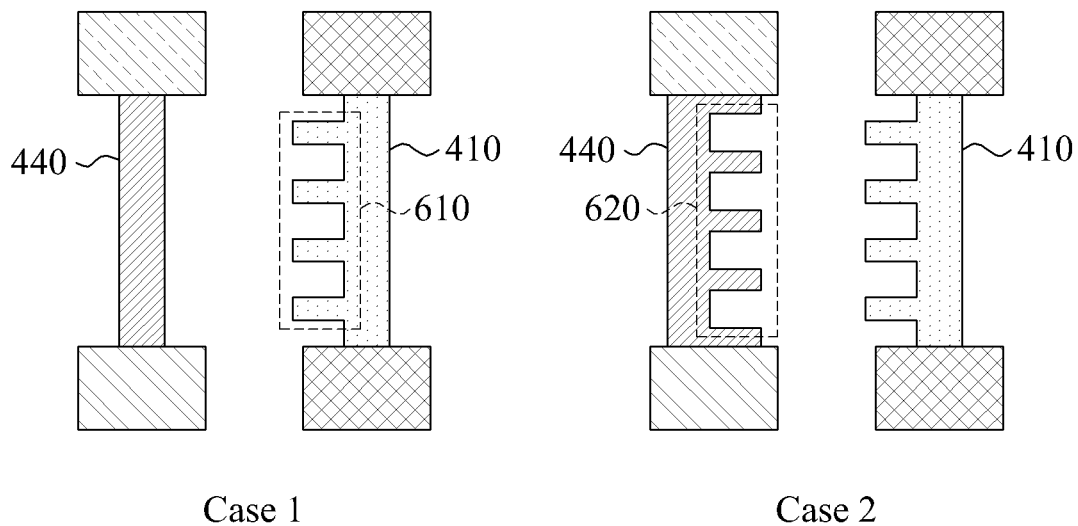
FIG. 6 is a diagram illustrating examples of a nanowire and a gate electrode of the nano resonance apparatus of FIG. 4

FIG. 6 is a diagram illustrating examples of the nanowire and the gate electrode of the nano resonance apparatus of FIG. 4. The gate electrode 410 includes a protruding portion 610 having a shape of a comb-like polygon to increase a surface area of the gate electrode 410 facing the nanowire 440.

As shown in Case 1, the nanowire 440 does not include a protruding portion or an indented portion.

As shown in Case 2, the nanowire 440 includes an indented portion 620 corresponding to the protruding portion 610 of the gate electrode 410 to increase a surface area of the nanowire 440 facing the gate electrode 410.

Figure 7:
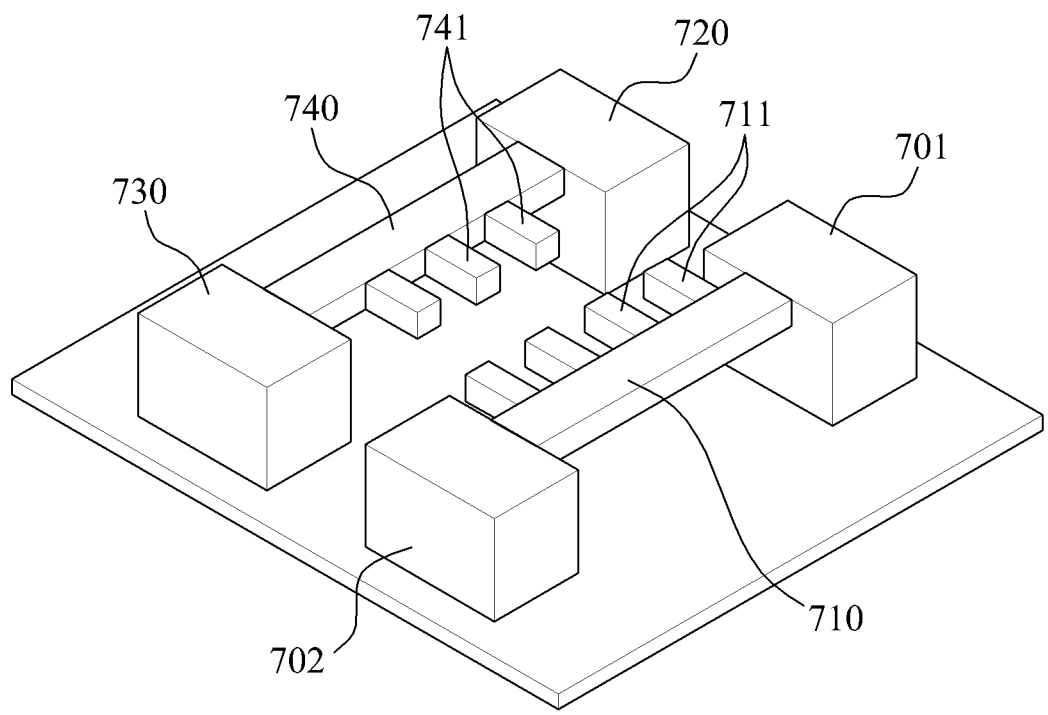
FIG. 7 is a diagram illustrating another example of a structure of a nano resonance apparatus.

FIG. 7 is a diagram illustrating another example of a structure of a nano resonance apparatus. Referring to FIG. 7, the nano resonance apparatus includes a gate electrode 710, a source electrode 720, a drain electrode 730, and a nanowire 740. The nano resonance apparatus of FIG. 7 is a combination of a vibrating body type nano resonator and a suspended gate type nano resonator.

The gate electrode 710 includes at least one protruding portion 711 extending in a direction of the nanowire 740 to increase a surface area of the gate electrode 710 facing the nanowire 740. The at least one protruding portion 711 may have a shape of at least one polygon or at least one curve. The shape of the at least one protruding portion 711 will be described in further detail with reference to FIG. 9.

The gate electrode 710 generates a magnetic field, and vibrates with the nanowire 740 in the presence of the magnetic field. To enable the vibration of the gate electrode 710 with the nanowire 740 in the presence of the magnetic field, the gate electrode 710 is spaced a predetermined distance or more apart from a substrate on which the source electrode 720 and the drain electrode 730 are disposed. A supporting unit is provided on the substrate to support the gate electrode 710 at the predetermined distance or more apart from the substrate.

In the example in FIG. 7, the supporting unit includes a first supporting unit 701 and a second supporting unit 702.

The nanowire 740 connects the source electrode 720 to the drain electrode 730. The nanowire 740 includes at least one protruding portion 741 forming at least one indented portion corresponding to the at least one protruding portion 711 of the gate electrode 710 to increase a surface area of the nanowire 740 facing the gate electrode 710, and vibrates with the gate electrode 710 in the presence of the magnetic field generated by the gate electrode 710. In the example in FIG. 7, the at least one protruding portion 711 of the gate electrode 710 has a shape of a comb-like polygon having teeth, and the at least one protruding portion 741 of the nanowire 740 has a shape of a comb-like polygon having teeth that alternate with the teeth of the comb-like polygon of the at least one protruding portion 711 of the gate electrode 710.

Instead of the at least protruding portion 741, the nanowire 740 may include at least one indented portion corresponding to the at least one protruding portion 711 of the gate electrode 710.

The at least one protruding portion 741 of the nanowire 740 may have a shape of at least one polygon or at least one curve. The shape of the at least one protruding portion 741 will be described in further detail with reference to FIG. 9.

Alternatively, the nanowire 740 may include a protruding portion, and the gate electrode 710 may include an indented portion corresponding to the protruding portion of the nanowire 740.

Figure 8:
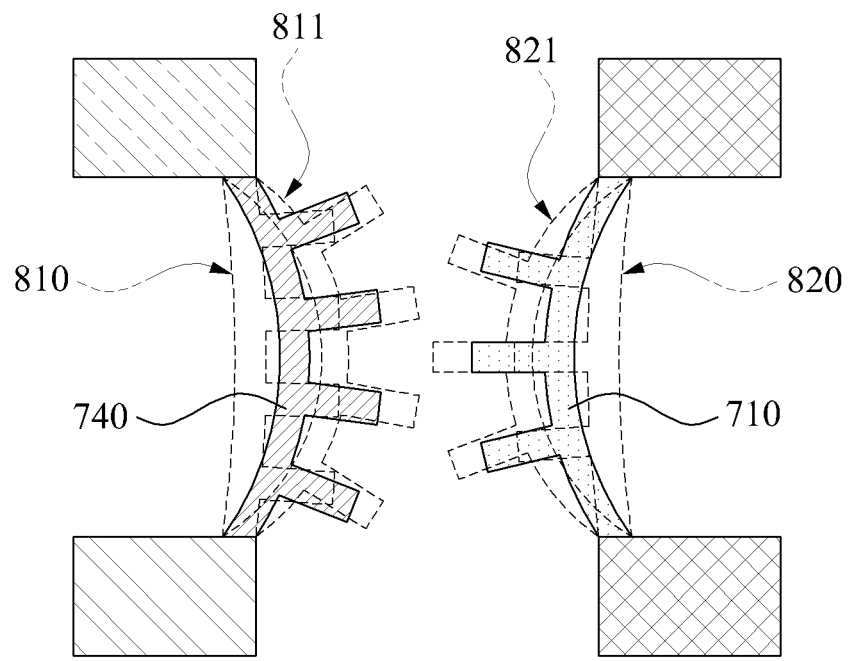
FIG. 8 is a diagram illustrating an example of operation of the nano resonance apparatus of FIG. 7.

FIG. 8 is a diagram illustrating an example of operation of the nano resonance apparatus of FIG. 7. The gate electrode 710 of the nano resonance apparatus generates a magnetic field, and vibrates with the nanowire 740 in the presence of the magnetic field. The gate electrode 710 is alternately attracted to the nanowire 740 as indicated by reference numeral 821, and repelled from the nanowire 740 as indicated by reference numeral 820, due to the presence of the magnetic field. The nanowire 740 is alternately attracted to the gate electrode 710 as indicated by reference numeral 811, and repelled from the gate electrode 710 as indicated by reference numeral 810, due to the presence of the magnetic field.

The gate electrode 710 and the nanowire 740 vibrate with each other with an increased sensitivity in the presence of the magnetic field generated by the gate electrode 710 due to the increased surface area of the gate electrode 710 facing the nanowire 740 caused by the at least one protruding portion 711 of the gate electrode 710, and the increased surface area of the nanowire 740 facing the gate electrode 710 caused by the at least one protruding portion 741 of the nanowire 740.

Figure 9:
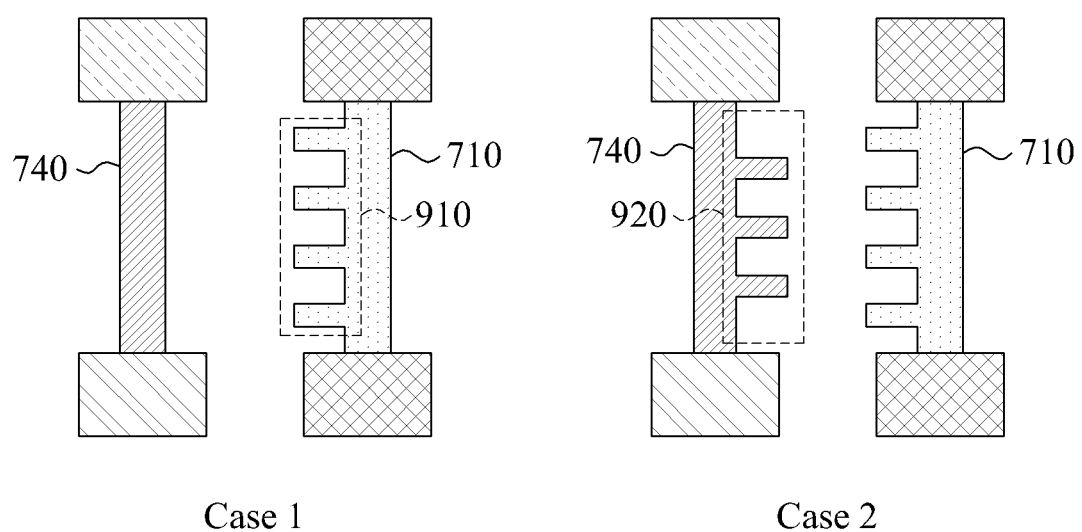
FIG. 9 is a diagram illustrating examples of a nanowire and a gate electrode of the nano resonance apparatus of FIG. 7.

FIG. 9 is a diagram illustrating examples of the nanowire and the gate electrode of the nano resonator of FIG. 7. The gate electrode 710 includes a protruding portion 910 having a shape of a comb-like polygon to increase a surface area of the gate electrode 710 facing the nanowire 740.

As shown in Case 1, the nanowire 740 does not include a protruding portion or an indented portion.

As shown in Case 2, the nanowire 740 includes a protruding portion 920 forming an indented portion corresponding to the protruding portion 910 of the gate electrode 710 to increase a surface area of the nanowire 740 facing the gate electrode 710.

Figure 10:
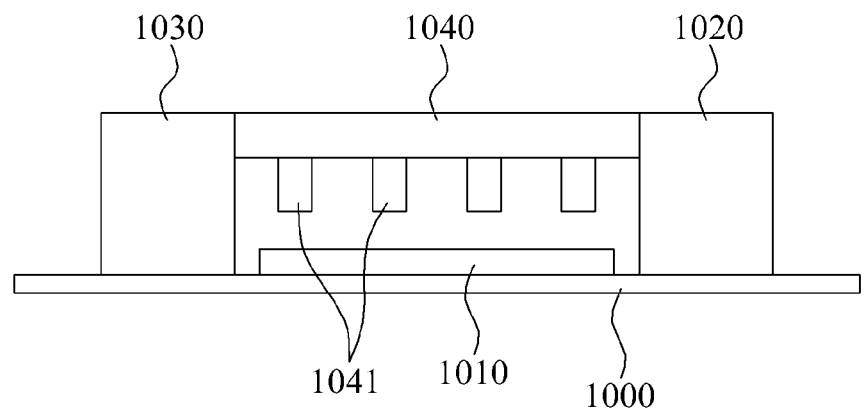
FIG. 10 is a diagram illustrating another example of a structure of a nano resonance apparatus.

FIG. 10 is a diagram illustrating another example of a structure of a nano resonance apparatus. Referring to FIG. 10, the nano resonance apparatus includes a gate electrode 1010, a source electrode 1020, a drain electrode 1030, and a nanowire 1040. The gate electrode 1010 is located at a predetermined distance below the nanowire 1040, and is disposed between the nanowire 1040 and a substrate 1000 on which the source electrode 1020 and the drain electrode 1030 are disposed. The gate electrode 1010 generates a magnetic field.

The nanowire 1040 connects the source electrode 1020 to the drain electrode 1030, and vibrates in the presence of the magnetic field generated by the gate electrode 1010. The nanowire 1040 includes at least one protruding portion 1041 extending down in a direction toward the gate electrode 1010 to increase a surface area of the nanowire 1040 facing the gate electrode 1010. When resonance occurs, the nanowire 1040 vibrates in a vertical direction toward and away from the gate electrode 1010.

The gate electrode 1010 does not include a protruding portion or an indented portion. Alternatively, the gate electrode 1010 may include an indented portion corresponding to the protruding portion 1041 of the nanowire 1040 to increase a surface area of the gate electrode 1010 facing the nanowire 1040. The protruding portion 1041 of the nanowire 1040 may have a shape of at least one polygon or at least one curve.

Figure 11:
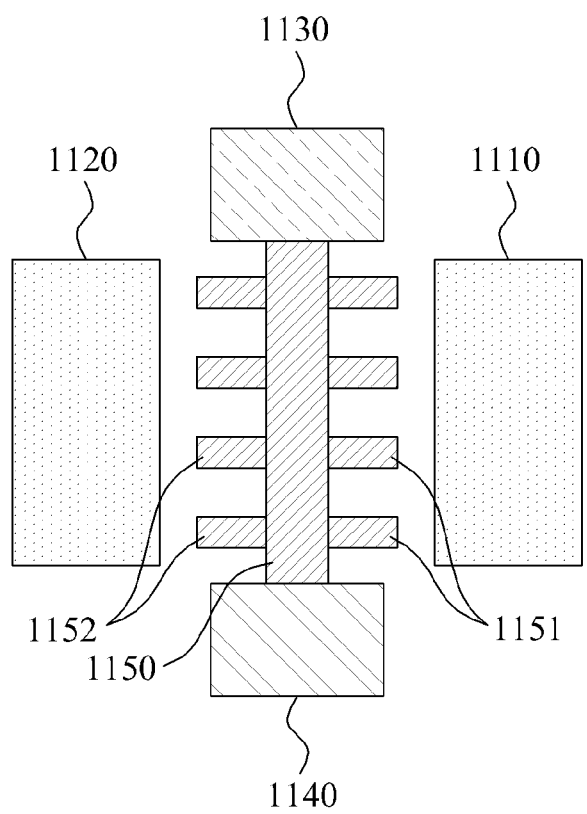
FIG. 11 is a diagram illustrating another example of a structure of a nano resonance apparatus.

FIG. 11 is a diagram illustrating another example of a structure of a nano resonance apparatus. Referring to FIG. 11, the nano resonance apparatus includes a first gate electrode 1110, a second gate electrode 1120, a source electrode 1130, a drain electrode 1140, and a nanowire 1150. Thus, the nano resonance apparatus of FIG. 11 includes two gate electrodes.

The nanowire 1150 connects the source electrode 1130 to the drain electrode 1140, and vibrates in the presence of magnetic fields generated by the first gate electrode 1110 and the second gate electrode 1120. To enable the vibration of the nanowire 1150 in the presence of the magnetic fields generated by the first gate electrode 1110 and the second gate electrode 1120, the nanowire 1150 is spaced a predetermined distance or more apart from a substrate on which the source electrode 1130 and the drain electrode 1140 are disposed.

Different voltages and different signals may be applied to the first gate electrode 1110 and the second gate electrode 1120. The nano resonance apparatus may control the voltages and the signals applied to the first gate electrode 1110 and the second gate electrode 1120 to control a direction and a magnitude of vibration of the nanowire 1150 caused by resonance.

For example, the first gate electrode 1110 may be disposed in a diagonal direction relative to the nanowire 1150. In this case, when resonance occurs, the nanowire 1150 will vibrate in a diagonal direction toward and away from the first gate electrode 1110. When a higher voltage is applied to the first gate electrode 1110 than to the second gate electrode 1120, an amplitude of a vibration of the nanowire 1150 in the presence of the magnetic field generated by the first gate electrode 1110 will be larger than an amplitude of a vibration of the nanowire 1150 in the presence of the magnetic field generated by the second gate electrode 1120.

The nanowire 1150 includes at least one protruding portion 1151 extending in a direction of the first gate electrode 1110 to increase a surface area of the nanowire 1150 facing the first gate electrode 1110, and at least one protruding portion 1152 extending in a direction of the second gate electrode 1120 to increase a surface area of the nanowire 1150 facing the second gate electrode 1120. In the example in FIG. 11, the first gate electrode 1110 and the second first gate electrode 1120 do not include a protruding portion or an indented portion. However, the first gate electrode 1110 may include an indented portion corresponding to the at least one protruding portion 1151 of the nanowire 1150 to increase a surface area of the first gate electrode 1110 facing the nanowire 1150, and/or the second first gate electrode 1120 may include an indented portion corresponding to the at least one protruding portion 1152 of the nanowire 1150 to increase a surface area of the second gate electrode 1120 facing the nanowire 1150.

The protruding portions 1151 and 1152 of the nanowire 1150 may have a shape of at least one polygon or at least one curve.

The nano resonance apparatus improves a resonance sensitivity and a Q-factor by including the at least one protruding portion 1151 of the nanowire 1150 to increase a surface area of the nanowire 1150 facing the first gate electrode 1110, and the least one protruding portion 1152 of the nanowire 1150 to increase a surface area of the nanowire 1150 facing the second gate electrode 1120.

Figure 12:
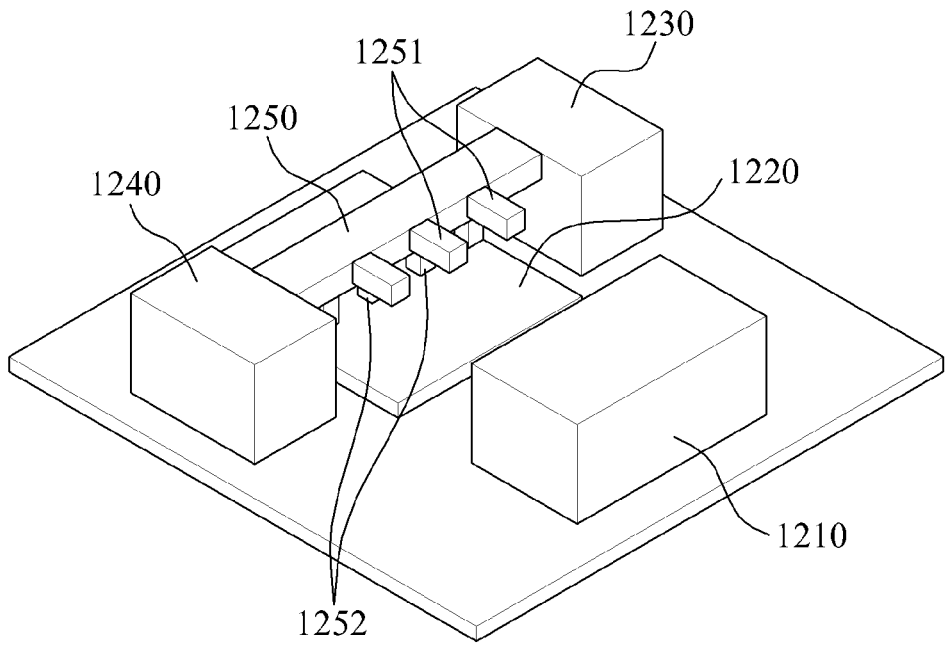
FIG. 12 is a diagram illustrating another example of a structure of a nano resonance apparatus.

FIG. 12 is a diagram illustrating another example of a structure of a nano resonance apparatus. Referring to FIG. 12, the nano resonance apparatus includes a first gate electrode 1210, a second gate electrode 1220, a source electrode 1230, a drain electrode 1240, and a nanowire 1250. Thus, the nano resonance apparatus of FIG. 12 includes two gate electrodes.

The nanowire 1250 connects the source electrode 1230 to the drain electrode 1240, and vibrates in the presence of magnetic fields generated by the first gate electrode 1210 and the second gate electrode 1220. To enable the vibration of the nanowire 1250 in the presence of the magnetic fields generated by the first gate electrode 1210 and the second gate electrode 1220, the nanowire 1250 is spaced a predetermined distance or more apart from a substrate on which the source electrode 1230 and the drain electrode 1240 are disposed.

Different voltages and different signals may be applied to the first gate electrode 1210 and the second gate electrode 1220. The nano resonance apparatus may control the voltages and the signals applied to the first gate electrode 1210 and the second gate electrode 1220 to control a direction and a magnitude of vibration of the nanowire 1250 caused by resonance.

When a higher voltage is applied to the first gate electrode 1210 than to the second gate electrode 1220, an amplitude of vibration of the nanowire 1250 in a horizontal direction toward and away from the first gate electrode 1210 will be larger than an amplitude of a vibration of the nanowire 1250 in a vertical direction toward and away from the second gate electrode 1220.

The nanowire 1250 includes at least one protruding portion 1251 extending in a direction of the first gate electrode 1210 to increase a surface area of the nanowire 1250 facing the first gate electrode 1210, and at least one protruding portion 1252 extending in a direction of the second gate electrode 1220 to increase a surface area of the nanowire 1250 facing the second gate electrode 1220. In the example in FIG. 12, the first gate electrode 1210 and the second first gate electrode 1220 do not include a protruding portion or an indented portion. However, the first gate electrode 1210 may include an indented portion corresponding to the at least one protruding portion 1251 of the nanowire 1250 to increase a surface area of the first gate electrode 1210 facing the nanowire 1250, and the second first gate electrode 1220 may include an indented portion corresponding to the at least one protruding portion 1252 of the nanowire 1250 to increase a surface area of the second gate electrode 1220 facing the nanowire 1250.

The protruding portions 1251 and 1252 of the nanowire 1250 may have a shape of at least one polygon or at least one curve.

The nano resonance apparatus improves a resonance sensitivity and a Q-factor by including the at least one protruding portion 1251 of the nanowire 1250 to increase a surface area of the nanowire 1250 facing the first gate electrode 1210, and the at least one protruding portion 1252 of the nanowire 1250 to increase a surface area of the nanowire 1250 facing the second gate electrode 1220.

Figure 13:
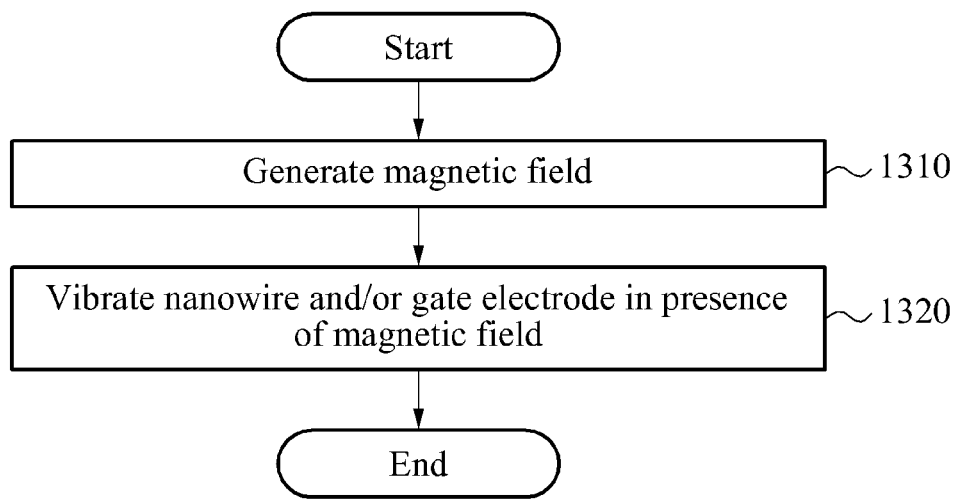
FIG. 13 is a flowchart illustrating an example of a nano resonance method.

FIG. 13 is a flowchart illustrating an example of a nano resonance method. Referring to FIG. 13, in operation 1310, a gate electrode of a nano resonance apparatus generates a magnetic field. When the nano resonance apparatus is a suspended gate type nano resonator or a combination of a vibrating body type nano resonator and a suspended gate type nano resonator, the gate electrode may include at least one protruding portion extending in a direction of a nanowire of the nano resonance apparatus to increase a surface area of the gate electrode facing the nanowire. When the nano resonance apparatus is a vibrating body type nano resonator or a combination of a vibrating body type nano resonator and a suspended gate type nano resonator, the nanowire may include at least one protruding portion extending in a direction of the gate electrode to increase a surface area of the nanowire facing the gate electrode.

In operation 1320, the nanowire of the nano resonance apparatus vibrates in the presence of the magnetic field generated in operation 1310. When the nano resonance apparatus is a vibrating body type nano resonator, the nanowire of the nano resonance apparatus vibrates in the presence of the magnetic field generated in operation 1310. When the nano resonance apparatus is a suspended gate type nano resonator, the gate electrode of the nano resonance apparatus vibrates in the presence of the magnetic field generated in operation 1310. When the nano resonance apparatus is a combination of a vibrating body type nano resonator and a suspended gate type nano resonator, the nanowire and the gate electrode of the nano resonance apparatus vibrate with one another in the presence of the magnetic field generated in operation 1310.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A nano resonance apparatus comprising:
   a gate electrode configured to generate a magnetic field; and
   a nanowire configured to connect a source electrode to a drain electrode, and configured to vibrate in the presence of the magnetic field,
   wherein the nanowire comprises a protruding portion extending in a direction of the gate electrode, the protruding portion configured to increase a surface area of the nanowire facing the gate electrode,
   wherein the gate electrode comprises an indented portion corresponding to the protruding portion of the nanowire, the indented portion configured to increase a surface area of the gate electrode facing the nanowire, and wherein the protruding portion of the nanowire is configured to vibrate in the presence of the magnetic field as the nanowire vibrates.

2. The nano resonance apparatus of claim 1, wherein the protruding portion has a shape of a polygon or a curve.

3. The nano resonance apparatus of claim 1, wherein the gate electrode is disposed adjacent to one side of the nanowire, or the gate electrode is one of a plurality of gate electrodes disposed adjacent to a plurality of sides of the nanowire.

4. The nano resonance apparatus of claim 1, wherein the nanowire is spaced a predetermined distance or more apart from a substrate on which the source electrode and the drain electrode are disposed.

5. The nano resonance apparatus of claim 4, wherein the gate electrode is disposed between the substrate and the nanowire.

6. A nano resonance apparatus comprising:
a nanowire configured to connect a source electrode to a drain electrode; and
a gate electrode configured to generate a magnetic field and to vibrate with the nanowire in the presence of the magnetic field,
wherein the gate electrode comprises a protruding portion extending in a direction of the nanowire, the protruding portion configured to increase a surface area of the gate electrode facing the nanowire, and
wherein the nanowire comprises an indented portion corresponding to the protruding portion of the gate electrode, the indented portion configured to increase a surface area of the nanowire facing the gate electrode.

7. A nano resonance apparatus comprising:
a gate electrode configured to generate a magnetic field; and
a nanowire configured to connect a source electrode to a drain electrode, and configured to vibrate with the gate electrode in the presence of the magnetic field;
wherein the gate electrode comprises a protruding portion extending in a direction of the nanowire, the protruding portion configured to increase a surface area of the gate electrode facing the nanowire, and
wherein the nanowire comprises an indented portion corresponding to the protruding portion of the gate electrode, the indented portion configured to increase a surface area of the nanowire facing the gate electrode.

8. A nano resonance apparatus comprising:
a gate electrode configured to generate a magnetic field; and
a nanowire configured to connect a source electrode to a drain electrode, and configured to vibrate with the gate electrode in the presence of the magnetic field,
wherein the nanowire comprises a protruding portion extending in a direction of the gate electrode, the protruding portion configured to increase a surface area of the nanowire facing the gate electrode, and
wherein the gate electrode comprises an indented portion corresponding to the protruding portion of the nanowire, the indented portion configured to increase a surface area of the gate electrode facing the nanowire.

9. A nano resonance method performed by a nano resonance apparatus, the method comprising:
generating a magnetic field using a gate electrode of the nano resonance apparatus; and
vibrating a nanowire of the nano resonance apparatus in the presence of the magnetic field;
wherein the nanowire comprises a protruding portion extending in a direction of the gate electrode, the protruding portion configured to increase a surface area of the nanowire facing the gate electrode,
wherein the gate electrode comprises an indented portion corresponding to the protruding portion of the nanowire, the indented portion configured to increase a surface area of the gate electrode facing the nanowire, and
wherein the protruding portion of the nanowire vibrates in the presence of the magnetic field as the nanowire vibrates.

10. A nano resonance method performed by a nano resonance apparatus, the method comprising:
generating a magnetic field using a gate electrode of the nano resonance apparatus; and
vibrating the gate electrode of the nano resonance apparatus in the presence of the magnetic field;
wherein the gate electrode comprises a protruding portion extending in a direction of a nanowire of the nano resonance apparatus to increase a surface area of the gate electrode facing the nanowire, and
wherein the nanowire comprises an indented portion corresponding to the protruding portion of the gate electrode, the indented portion configured to increase a surface area of the nanowire facing the gate electrode.

11. A nano resonance method performed by a nano resonance apparatus, the method comprising:
generating a magnetic field using a gate electrode of the nano resonance apparatus; and
vibrating the gate electrode of the nano resonance apparatus with a nanowire of the nano resonance apparatus in the presence of the magnetic field;
wherein the gate electrode comprises a protruding portion extending in a direction of the nanowire, the protruding portion configured to increase a surface area of the gate electrode facing the nanowire, and
wherein the nanowire comprises an indented portion corresponding to the protruding portion of the gate electrode, the indented portion configured to increase a surface area of the nanowire facing the gate electrode.

12. A nano resonance method performed by a nano resonance apparatus, the method comprising:
generating a magnetic field using a gate electrode of the nano resonance apparatus; and
vibrating a nanowire of the nano resonance apparatus with the gate electrode of the nano resonance apparatus in the presence of the magnetic field;
wherein the nanowire comprises a protruding portion extending in a direction of the gate electrode, the protruding portion configured to increase a surface area of the nanowire facing the gate electrode, and
wherein the gate electrode comprises an indented portion corresponding to the protruding portion of the nanowire, the indented portion configured to increase a surface area of the gate electrode facing the nanowire.

13. A nano resonance apparatus comprising:
a gate electrode configured to generate a magnetic field; and
a nanowire;
wherein the gate electrode comprises a protruding portion extending in a direction of the nanowire, the protruding portion configured to increase a surface area of the gate electrode facing the nanowire, and wherein the nanowire comprises an indented portion corresponding to the protruding portion of the gate electrode, the indented portion configured to increase a surface area of the nanowire facing the gate electrode, or
wherein the nanowire comprises a protruding portion extending in a direction of the gate electrode, the protruding portion configured to increase a surface area of the nanowire facing the gate electrode, and wherein the gate electrode comprises an indented portion corresponding to the protruding portion of the nanowire, the indented portion configured to increase a surface area of the gate electrode facing the nanowire.

14. The nano resonance apparatus of claim 13,
wherein the nanowire is configured to vibrate in the presence of the magnetic field, and the gate electrode is configured to not vibrate in the presence of the magnetic field, or
wherein the gate electrode is configured to vibrate in the presence of the magnetic field, and the nanowire is configured to not vibrate in the presence of the magnetic field, or
wherein the nanowire and the gate electrode are configured to vibrate with one another in the presence of the magnetic field.

15. The nano resonance apparatus of claim 13, further comprising:
a source electrode; and
a drain electrode;
wherein the nanowire connects the source electrode to the drain electrode.

16. The nano resonance apparatus of claim 13,
wherein the gate electrode is a first gate electrode;
wherein the nano resonance apparatus further comprises a second gate electrode; and
wherein the first gate electrode is spaced apart from the nanowire in a first direction, and the second gate electrode is spaced apart from the nanowire in a second direction substantially opposite to the first direction, or
wherein the first gate electrode is spaced apart from the nanowire in a first direction, and the second gate electrode is spaced apart from the nanowire in a second direction substantially perpendicular to the first direction.

* * * * *